United States Patent
Kang et al.

(10) Patent No.: US 8,379,212 B2
(45) Date of Patent: Feb. 19, 2013

(54) PLASMONIC DROPLET, METHOD AND APPARATUS FOR PREPARING THE SAME, DETECTION METHOD USING PLASMONIC DROPLET

(75) Inventors: Taewook Kang, Seoul (KR); Luke P. Lee, Orinda, CA (US); Yeonho Choi, Seoul (KR); Younggeun Park, Incheon (KR)

(73) Assignees: Industry-University Cooperation Foundation Sogang University, Seoul (KR); University of California, Berkeley, Berkeley, CA (US)

(*) Notice: Subject to any disclaimer, the term of this patent is extended or adjusted under 35 U.S.C. 154(b) by 340 days.

(21) Appl. No.: 12/755,743

(22) Filed: Apr. 7, 2010

(65) Prior Publication Data
US 2011/0249267 A1    Oct. 13, 2011

(51) Int. Cl.
    *G01N 21/55* (2006.01)
(52) U.S. Cl. .................................................. 356/445
(58) Field of Classification Search ................ None
    See application file for complete search history.

(56) References Cited

U.S. PATENT DOCUMENTS

| | | | |
|---|---|---|---|
| 2009/0020426 A1* | 1/2009 | Thundat et al. | 204/450 |
| 2010/0323906 A1* | 12/2010 | Chen et al. | 506/9 |

* cited by examiner

*Primary Examiner* — Tu Nguyen
(74) *Attorney, Agent, or Firm* — Sughrue Mion PLLC

(57) ABSTRACT

Disclosed herein is an innovative plasmonic droplet including a droplet of fluid, a detection-target material which is in the droplet of fluid, and a nanoplasmon probe which is on a surface of the droplet of fluid and/or in the droplet of fluid. The plasmonic droplet may be applied for plasmon based optical sensing techniques, for example, for ultrasensitive analysis of bacteria, pathogen, etc.

14 Claims, 6 Drawing Sheets ered image, scattered intensity, image id # PLASMONIC DROPLET, METHOD AND APPARATUS FOR PREPARING THE SAME, DETECTION METHOD USING PLASMONIC DROPLET

BACKGROUND

1. Field

This disclosure relates to a plasmonic droplet, a method and apparatus for preparing the same, a detection method using the palsmonic droplet.

2. Description of the Related Art

Optical absorption energy spectroscopy at visible wavelength range is a common analytical method in chemistry and biology since it has merits such as simplicity in measuring and data processing, wide usuage, non-tagged analysis, etc.

Probes used in most optical systems so far have been developed primarily based on organic reporters which are detected by a change of color or fluorescence emission spectrum.

Meanwhile, plasmon based optical sensing techniques such as localized surface plasmon resonance (LSPR), surface enhanced raman scattering (SERS), plasmon resonance energy transfer (PRET) etc. have been studied.

The plasmon based optical sensing techniques use surface plasmonic resonance which occurs when light is confined within a metal surface due to interaction with free-electrons in the metal.

In general, as the plasmon based optical sensing techniques take advantage of locally enhanced electromagnetic field by the incident light-metal interaction in very small length scale, the sensitivity and selectivity can be dramatically improved. Furthermore, in the techniques, spatial resolution can be minimized by shrinking the detection site.

SUMMARY

Disclosed herein is in an embodiment a plasmonic droplet including a droplet of fluid; a detection-target material which is in the droplet of fluid; and a nanoplasmon probe which is on a surface of the droplet of fluid and/or in the droplet of fluid.

In an example embodiment, the droplet of fluid is a droplet of a first fluid which is in an emulsion of the first fluid and a second fluid.

In an example embodiment, the plasmonic droplet further includes a layer of a surfactant on the surface of droplet of fluid and the nanoplasmon probe is on the layer of the surfactant and/or in the droplet of fluid.

In an example embodiment, two or more plasmonic droplets are arranged to constitue an array of the plasmonic droplet.

Disclosed herein is in an embodiment a method for preparing a plasmonic droplet including: providing a micro-fluid flow of a second fluid with a micro-fluid flow of a first fluid including a nanoplasmon probe and a detection-target material, thereby forming a plasmonic droplet, wherein the first fluid and the second fluid are able to form an emulsion, and the plasmonic droplet includes a droplet of the first fluid; a detection-target material which is in the droplet of the first fluid; and a nanoplasmon probe which is on a surface of the droplet of the first fluid and/or in the droplet of the first fluid.

In an example embodiment, the first fluid further includes a surfactant.

In an example embodiment, the method further includes reducing a size of the plasmonic droplet to the extent that the nanoplasmon probe is attached to the detection-target material.

In an example embodiment, the method further includes changing a size of the plasmonic droplet by changing a pressure of at least one of the micro-fluid of the first flow and the micro-fluid of the second flow.

In an example embodiment, the method further includes reducing a size of the plasmonic droplet by vaporizing the first fluid in the plasmonic droplet. The vaporizing may be conducted through light radiation to the plasmonic droplet.

In an example embodiment, the diameter of the plasmonic droplet is from about 15 micrometer to about 25 micrometer.

In an example embodiment, the second fluid has an oil phase and the first fluid is $H_2O$.

Disclosed herein is in an embodiment an apparatus for preparing a plasmonic droplet including: a second microfluid channel guiding a micro-fluid flow of a second fluid; and a first micro-fluid channel guiding a micro-fluid flow of a first fluid including a detection-target material and a nanoplasmon probe and providing the second micro-fluid channel with the micro-fluid flow of the first fluid, wherein the first fluid and the second fluid are able to form an emulsion, and the plasmonic droplet includes a droplet of the first fluid; a detection-target material which is in the droplet of the first fluid; and a nanoplasmon probe which is on a surface of the droplet of the first fluid and/or in the droplet of the first fluid.

In an example embodiment, the first fluid further includes a surfactant.

Disclosed herein is in an embodiment a method for detecting target material including providing a plasmonic droplet including a droplet of fluid; a detection-target material which is in the droplet of fluid; and a nanoplasmon probe which is on a surface of the droplet of fluid and/or in the droplet of fluid; reducing a size of the plasmonic droplet to the extent that the nanoplasmon probe is attached to the detection-target material; and performing plasmon based optical sensing with the plasmonic droplet where the nanoplasmon probe is attached to the detection-target material.

The plasmonic droplet according to the embodiments has a high detection throughput and is useful for the plasmon based optical sensing techniques such as techniques using localized surface plasmon resonance, surface enhanced raman scattering, plasmon resonance energy transfer, etc.

In particular, the plasmonic droplet according to the embodiments are useful for ultrasensitive analysis of bacteria, pathogen, etc.

BRIEF DESCRIPTION OF THE DRAWINGS

The above and other aspects, features and advantages of the disclosed example embodiments will be more apparent from the following detailed description taken in conjunction with the accompanying drawings in which:

FIG. 3 also shows the scattered images (Dark-field microscope image) of the respective droplets along with the scattered intensity. In FIG. 3, X axis represents a wavelength (unit: nm) and Y axis represents a scattered intensity (unit: arbitary unit)

In FIG. 4, X axis represents a wavelength (unit: nm) and Y axis represents a scattered intensity (unit: arbitrary unit)

In FIG. 6, X axis represents a Raman shift (unit: $cm^{-1}$) and Y axis represents a relative intensity (unit: arbatary unit)

DETAILED DESCRIPTION

Figure 1:
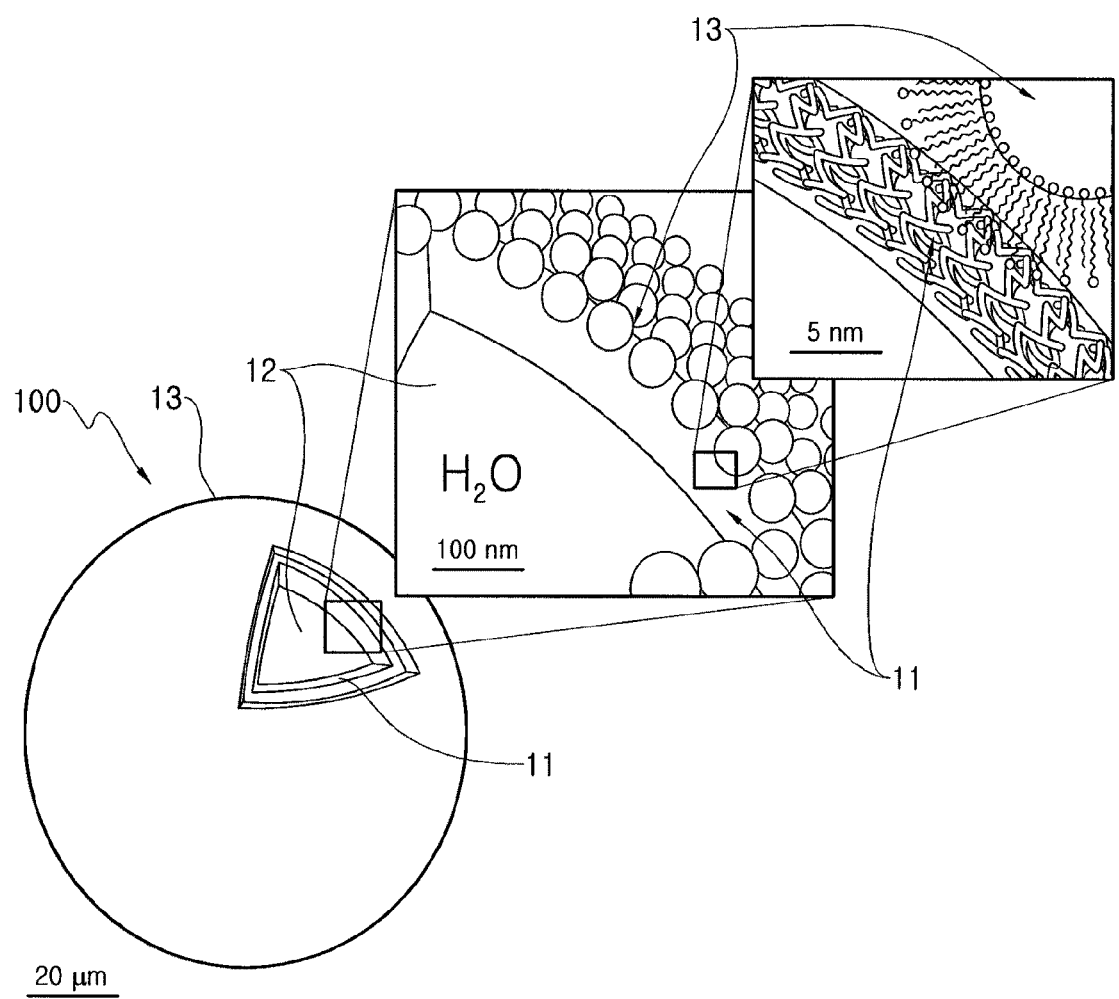
FIG. 1 is a schematic view illustrating a plasmonic droplet according to an example embodiment.
Figure 2:
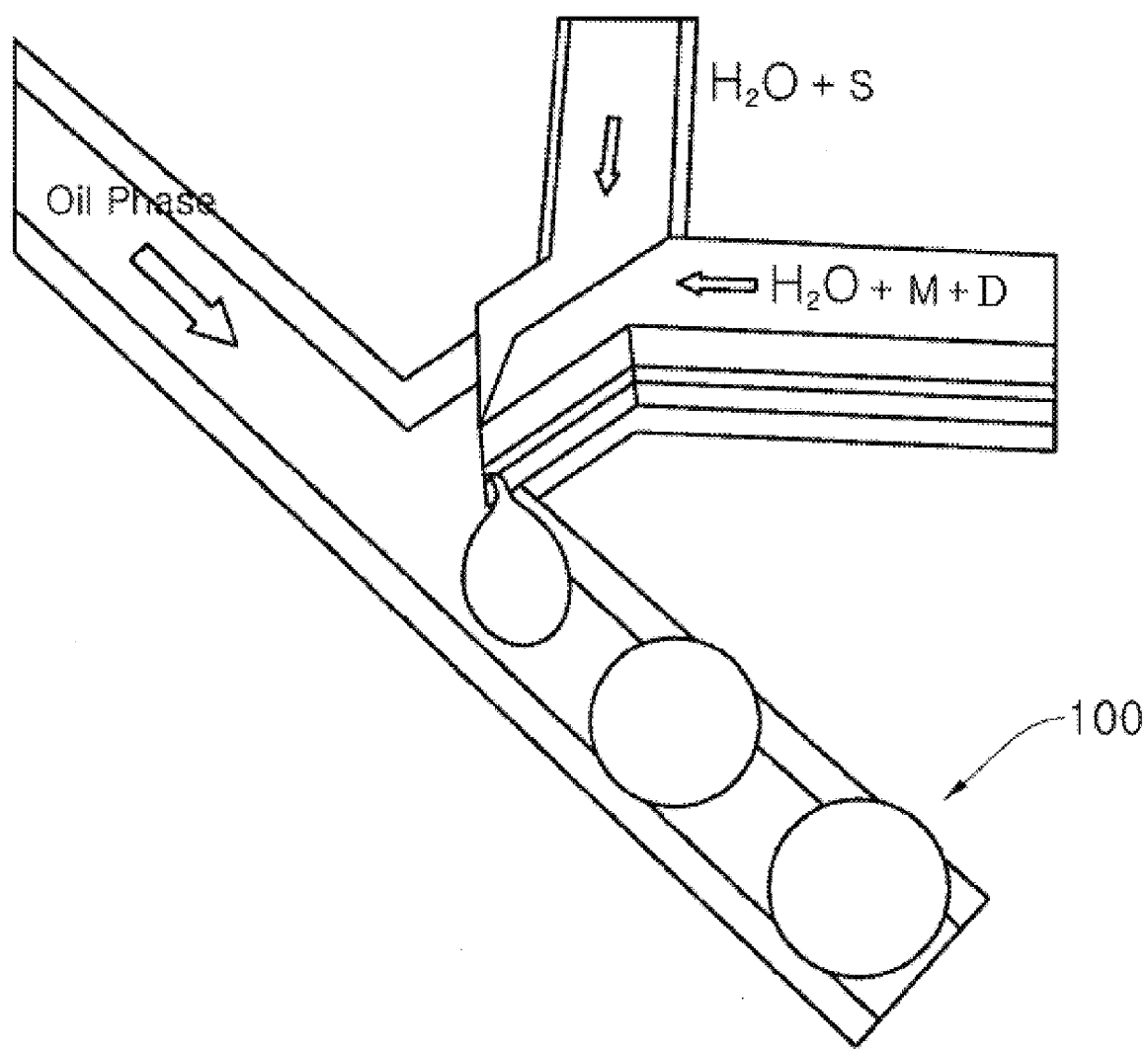
FIG. 2 is a schematic view illustrating the conception of a method and an apparatus for preparing the plasmonic droplet of FIG. 1.

Example embodiments are described more fully hereinafter. The invention may, however, be embodied in many different forms and should not be construed as limited to the Example embodiments set forth herein. Rather, these Example embodiments are provided so that this disclosure will be thorough and complete, and will fully convey the scope of the invention to those skilled in the art. In the description, details of features and techniques may be omitted to more clearly disclose Example embodiments.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. Spatially relative terms, such as "below", "lower", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly. The terminology used herein is for the purpose of describing particular embodiments only and is not intended to be limiting of the invention. As used herein, the singular forms "a," "an" and "the" are intended to include the plural forms as well, unless the context clearly indicates otherwise. Furthermore, the use of the terms a, an, etc. do not denote a limitation of quantity, but rather denote the presence of at least one of the referenced item. The terms "first," "second," and the like do not imply any particular order, but are included to identify individual elements. Moreover, the use of the terms first, second, etc. do not denote any order or importance, but rather the terms first, second, etc. are used to distinguished one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

In this context, nano size refers to a size of 100 nm or less.

In this context, a nanoplasmon probe refers to a nano-sized metal particle which is able to show a surface plasmonic resonance.

In this context, a detection-target material refers to a material to be detected by the nanoplasmon probes and includes but not limited to bacteria, pathogen, white cell, T cell, etc.

Surface plasmonic resonance occurs when light is confined within a metal surface due to interaction with free-electrons in the metal. The surface plasmonic resonance may increase electromagnetic field on the surface of the metal. When materials such as particles or molecules (for example, metal ions, DNA, proteins etc.) are put around the surface of metal showing the surface plasmonic resonance, the surface plasmonic resonance and the materials affect each other.

That is, the neighboring materials may be affected as if they are exposed to a strong electromagnetic field. Meanwhile, the resonance feature of metal surface may show a delegate change due to a variation of dielectric function induced by the neighboring materials.

Meanwhile, microfluidics deals with a behavior, precise control and manipulation of fluids that are geometrically constrained to a small, typically micro or mezzo scale. It is known to produce a small droplet of fluid itself, for example, using a micro-fluid channel based on the conception of micro fluidics.

Herein, the inventors associate the concept of nanoplasmonics with that of microfuidics. In an embodiment of the invention, based on the concepts, an innovative detecting method using an innovative detecting structure referred as plasmonic droplet is provided. The plasmonic droplet is expected to be very useful for the plasmon based optical sensing techniques based on nanoplasmonics.

Specifically, disclosed herein is in an embodiment a plasmonic droplet including a droplet of fluid, a detection-target material which is in the droplet of fluid and a nanoplasmon probe which is on a surface of the droplet of fluid and/or in the droplet of fluid. Furthermore, in an example embodiment, the plasmonic droplet may further include a layer of a surfactant on the surface of droplet of fluid and the nanoplasmon probe may be on the layer of the surfactant and/or in the droplet fluid.

FIG. 1 is a schematic view illustrating a plasmonic droplet according to an example embodiment.

Referring to FIG. 1, a plasmon droplet 100 according to an example embodiment may have the following structure. That is, the plasmon droplet 100 has a droplet of fluid 12 (non-limiting example of the fluid includes $H_2O$). The droplet of fluid 12 contains a detection-target material (non-limiting example of the detection-target material includes bacteria, pathogen, etc.). A surfactant layer 11 is on a surface of the droplet of fluid 12. Nanoplasmon probes 13 are on the surfactant layer 11. Although FIG. 1 shows that nanoplasmon probes 13 are on the surfactant layer 11, the nanoplasmon probes 13 may also be present in the droplet of fluid 12. The diameter of the plasmon droplet 100 may be from several micrometer to several tens of micrometer. Herein, in another example embodiment, the surfactant layer 11 may be absent between the surface of the droplet of fluid 12 and the nanoplasmon probes 13. That is, the nanoplasmon probes 13 may be directly formed on the surface of the droplet of fluid 12. However, it may be advantageous for the plasmon droplet to have the surfactant layer 11 in order to better form the surface of the droplet of fluid 12.

In an example embodiment, the nanoplasmon probes may be metal nanoplasmonic particles or metal nanoplasmonic particles with ligands combined thereto.

For reference, FIG. 1, as a non-limiting example, illustrates self-assembled polymer ligands are combined with a single nanoplasmonic particle.

Non-limiting examples of the metal used for the nanoplasmonic particle may include gold or silver, and gold is preferred. Size or shape of the nanoplasmonic particle is not limited. As for the non-limiting examples, the nanoplasmonic particle may be a spherical shape, and the diameter of nanoplasmonic particle may be about 1 nm to about 100 nm. The diameter of nanoplasmonic particle may be about 20 nm to about 50 nm in order to secure enough scattering light intensity.

As in a non-limiting examples, the nanoplasmon probe may be a probe for detecting metal ions. The nanoplasmon probe may be a single nanoplasmonic particle physically and/or chemically combined with ligands which are able to form metal-ligand complexes with the targeted metal ions, wherein plasmonic resonance energy transfer occurs between the single nanoplasmonic particle and the metal-ligand complexes. By investigating the occurrence of plasmon resonance energy transfer between target metal ions and the single nanoplasmonic particle, the target metal ions can be detected. Such nanoplasmon probe is disclosed in U.S. patent application Ser. No. 12/512,656, the contents of which in its entirety is incorporated herein by reference.

FIG. 2 is a schematic view illustrating the conception of a method and an apparatus for preparing the plasmonic droplet of FIG. 1.

Referring to FIGS. 1 and 2, a micro-fluid of a second fluid (non-limiting example includes oil) flows in a second channel, which is a micro-fluid channel. For reference, as in a non-limiting example of a micro-fluid channel, size (diameter) of the micro-fluid channel may be from several tens of micrometer to several hundreds of micrometer.

A first micro-fluid channel guiding a micro-fluid flow of a first fluid (non-limiting example includes $H_2O$) containing nanoplasmon probes M and a detection-target material D is connected to the second channel.

If necessary, the second micro-fluid channel may be further provided with a first fluid having a surfactant S (non-limiting examples includes a surfactant having a type of tri-block copolymer) as is illustrated in FIG. 2.

Accordingly, a droplet of the first fluid 12 containing a detection-target material may be formed in the micro-fluid flow of the second fluid, a surfactant layer 11 may be formed on a surface of the droplet of the first fluid 12, nanoplasmon probes 13 may be formed on the surfactant layer 11 and/or be present in the droplet of the first fluid 12, thereby forming the plasmon droplet 100 as illustrated in FIG. 1.

Herein, as explained above referring to FIG. 1, by not providing the first fluid containing surfactants S, the nanoplasmon probes 13 may be directly formed on the surface of the droplet of the first fluid 12 without the surfactant layer 11 in the plasmon droplet 100.

In an embodiment for detecting target material, the plasmonic droplet as explained above is reduced to have such a size that the nanoplasmon probe, which is on a surface of the droplet of fluid and/or is dispersed in the droplet of fluid, is attached to the detection-target material in the droplet of fluid. This may mean that the size of the plasmonic droplet becomes similar to that of the detection-target material. Given that the nanoplasmon probe is attached to the detection-target material, plasmon based optical sensing techniques are performed to detect the target material. These plasmon based optical sensing techniques per se are known techniques and may include techniques using the localized surface plasmon resonance (LSPR), the surface enhanced raman scattering (SERS), the plasmon resonance energy transfer (PRET) etc.

In an example embodiment, the size of the plasmonic droplet may be changed by changing a pressure of at least one of the micro-fluid of the first flow and the micro-fluid of the second flow.

In an example embodiment, the size of the plasmonic droplet may be reduced by vaporizing the first fluid (e.g. $H_2O$) in the plasmonic droplet. The vaporizing may be conducted with the heat occurred through a light radiation.

In an example embodiment, the diameter of the plasmonic droplet may be from about 15 micrometer to about 25 micrometer.

In an example embodiment, two or more plasmonic droplets may be arranged to constitue an array of the plasmonic droplet. As in non-limiting example, the array may be an array where plasomon droplets are repeated continuously with a certain interval. The array of the plasomon droplets may increase the detection efficiency of the plasmon droplets by increasing the possibility that the plasmon droplets catch more detection-target materials. Such an array may be advantageous for high-speed detection and analysis of target materials such as bacteria, pathogen, etc.

The examples and experiments will now be described. The following examples and experiments are for illustrative purposes only and not intended to limit the scope of the present invention.

Micro-fluid channels and making a droplet of fluid per se are known. Herein, known micro-fluid channels may be adopted for a second micro-fluid channel and a first micro-fluid channel (refer to FIG. 2) (A diameter of the first and second micro-fluid channel may be about 50 micrometer). In the second micro-fluid channel, oil phase (herein oleic acid; instead mineral oil, soy bean oil, etc. may be used) flows. In the first micro-fluid channel, pure water having gold nanoplasmonic particles and detection-target bateria [proteus vulgaris (gram positive), pseudomonas fluorescence (gram positive), micrococcus luteus (gram negative), streptococcus lactis (gram negative); also refer to FIG. 6] flows. The gold nanoplasmonic particles used herein are about 50 nm in diameter. The pure water having gold nanoplasmonic particles and detection-target bateria is provided to the oil phase in the second micro-fluid channel, and pure water having surfactant (water-soluble triblock copolymer of the Pluronic class) is also provided to the second micro-fluid channel, thereby forming a plasmonic droplet (refer to FIG. 1). As a comparison, the droplet of water without gold nanoplasmonic particles are made.

Figure 3:
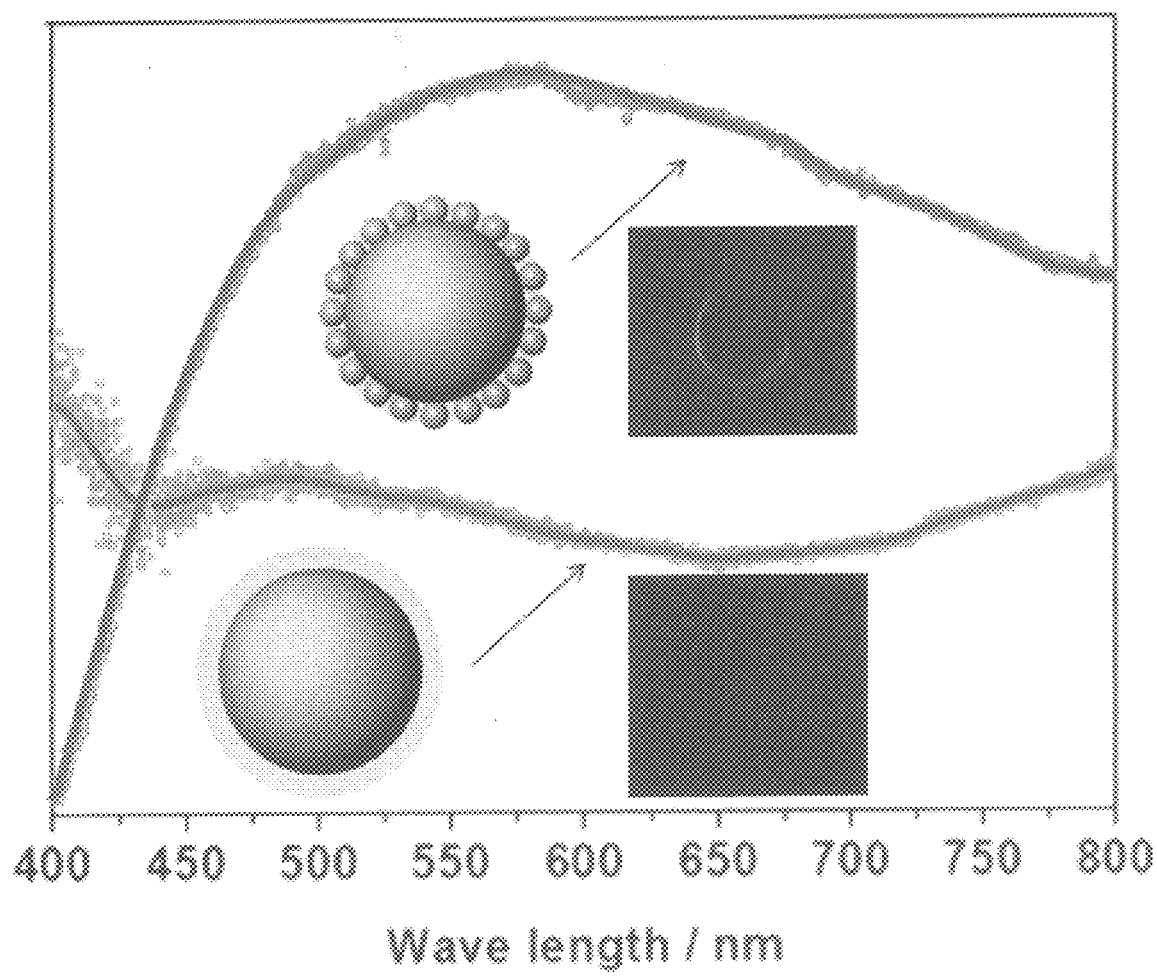
FIG. 3 is a graph showing a scattered intensity of a plasmonic droplet with nanoplasmon probes on a surface of droplete of $H_2O$ according to an example embodiment as compared to that of a droplet of $H_2O$ without nanoplasmon probes, depending on a wavelength.

FIG. 3 is a graph showing a scattered intensity of a plasmonic droplet with gold nanoplasmonic particles on a surface of droplet of $H_2O$ according to the example as compared to that of a droplet of $H_2O$ without gold nanoplasmonic particles, depending on a wavelength. FIG. 3 also shows the scattered images (Dark-field microscope image) of the respective droplets along with the scattered intensity. In FIG. 3, X axis represents a wavelength (unit: nm) and Y axis represents a scattered intensity (unit: arbitary unit)

A dark-field microscopy system may consist of a Carl Zeiss Axiovert 200 inverted microscope (Carl Zeiss) equipped with a dark-field condenser (NA 1.2~1.4), a true-colour digital camera (CoolSNAP cf, Roper Scientific), and monochromator (300 mm focal length and 300 grooves per mm, Acton Research) with a 1024×256 pixel cooled spectrograph CCD camera (Roper Scientific).

Referring to FIG. 3, the plasmon droplet with gold nanoplasmonic particles, i.e., the nanoplasmonic probes shows higher scattered intensity than that of droplet without nanoplasmonic probes.

Next, a size of the plasmon droplet is controlled. As explained above, the size of the plasmon droplet may be controlled in two ways. The first way is the pressure changing (i.e. changing pressure of the respective micro-fluid in the process of making the plasmon droplet), and the second way is vaporizing of the first fluid, water here, in the plasmon droplet, for example, through a laser light radiation.

Herein, with the second vaporizing method, the size of the plasmon droplet is controlled to have a diameter of about 25 micrometer, about 23 micrometer, about 20 micrometer and about 15 micrometer.

Figure 4:
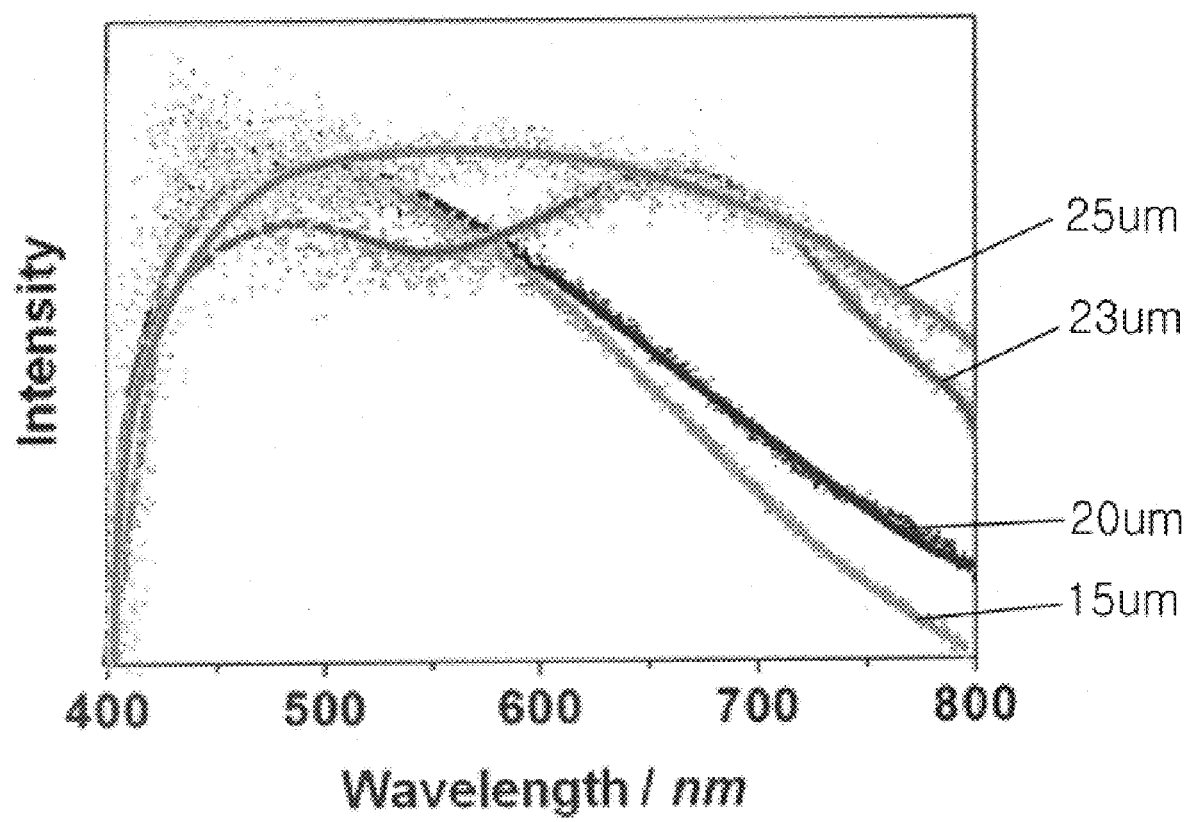
FIG. 4 is a graph showing a scattered intensity of plasmonic droplets having diverse sizes depending on a wavelength.

FIG. 4 is a graph showing a scattered intensity of plasmonic droplets having diverse sizes, depending on a wavelength. In FIG. 4, X axis represents a wavelength (unit: nm) and Y axis represents a scattered intensity (unit: arbitary unit)

An array of the plasmon droplets may be prepared. The array may be useful for a high-speed detection and analysis of the detection-target materials such as bacteria, pathogen, etc.

Figure 5A:
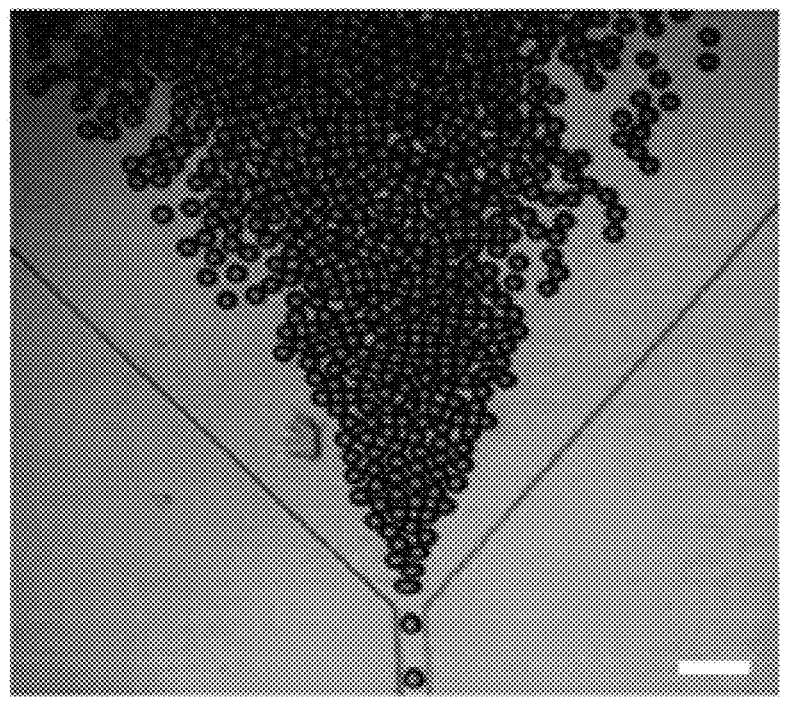
FIG. 5a is an image (Dark-field microscope image) illustrating an example view of generation of plasmonic droplets for forming an array.
Figure 5B:
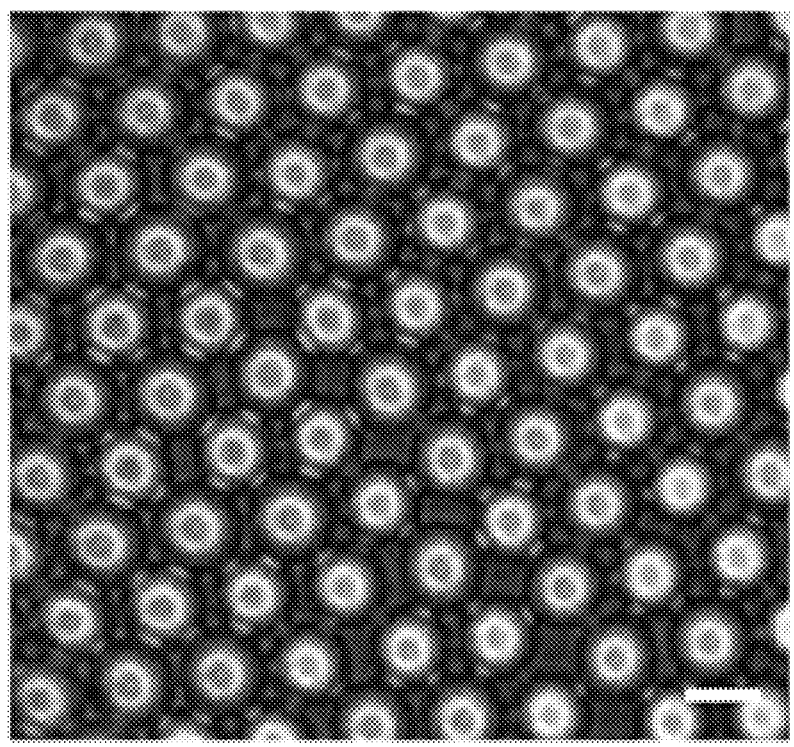
FIG. 5b is an image (Dark-field microscope image) illustrating an example view of formed array of plasmonic droplets.

FIG. 5a is an image (Dark-field microscope image) illustrating an example view of generation of plasmonic droplets for forming an array. FIG. 5b is an image (Dark-field microscope image) illustrating an example view of formed array of plasmonic droplets.

[Bacteria detection] As explained above, by vaporizing water in the plasmonic droplet, its size is reduced to be similar with the size of bacteria. This means that the gold nanoplasmonic particles become attached to bacteria. Herein, Surface enhanced raman scattering (SERS) is performed. As a result, membrane protein of the respective bacteria is detected.

Figure 6:
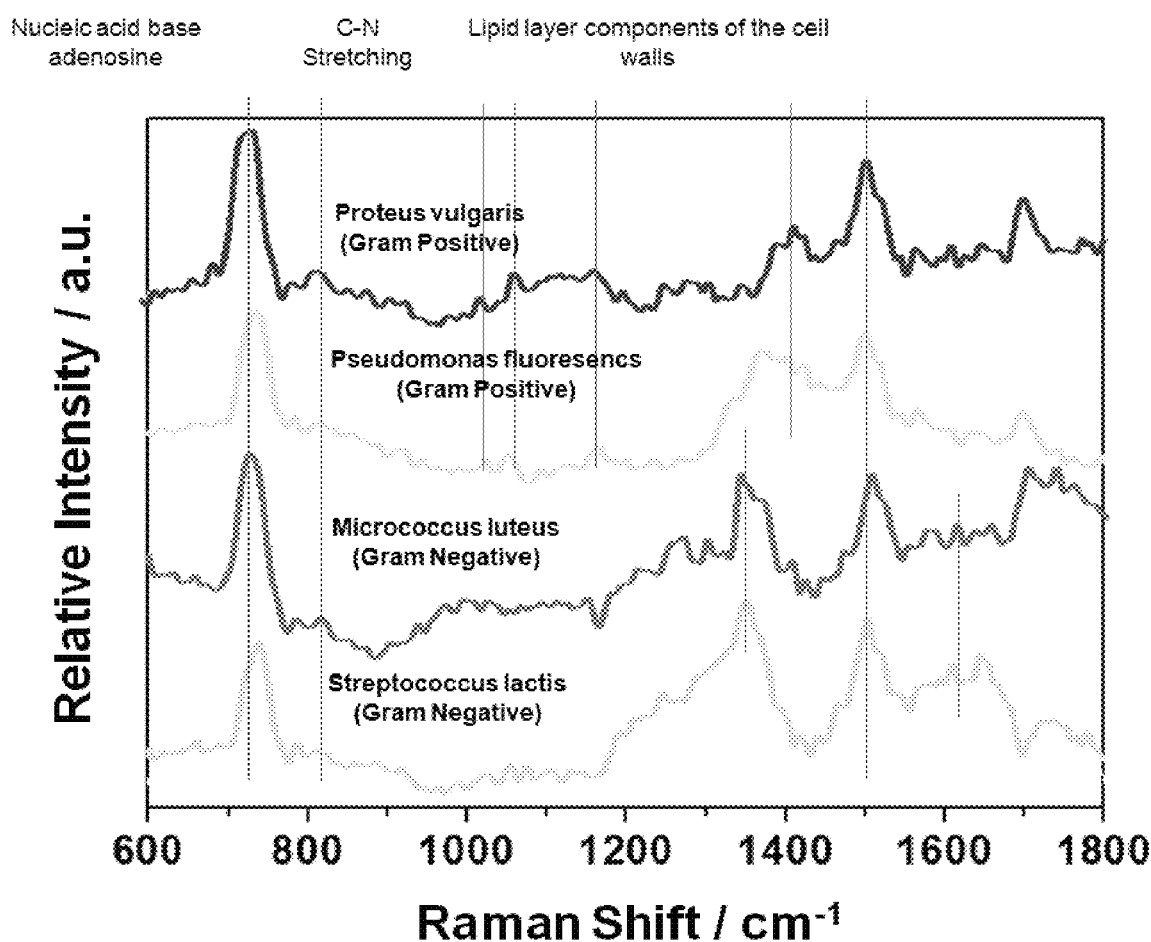
FIG. 6 is a graph showing the membrane protein of the respective bacteria is detected when performing surface enhanced raman scattering (SERS) using the plasmonic droplet.

FIG. 6 is a graph showing the membrane protein of the respective bacteria [proteus vulgaris (gram positive), pseudomonas fluorescence (gram positive), micrococcus luteus (gram negative), streptococcus lactis (gram negative)] is detected when performing surface enhanced raman scattering (SERS) using the plasmonic droplet. In FIG. 6, X axis represents a Raman shift (unit: $cm^{-1}$) and Y axis represents a relative intensity (unit: arbitary unit)

While the invention has been shown and described with reference to certain Example embodiments thereof, it will be understood by those skilled in the art that various changes in form and details may be made thereto without departing from the spirit and scope of the invention as defined by the appended claims.

In addition, modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A plasmonic droplet, comprising:
    a droplet of fluid;
    a detection-target material which is in the droplet of fluid; and
    a nanoplasmon probe which is on a surface of the droplet of fluid and/or in the droplet of fluid,
    wherein the detection-target material is to be detected by the nanoplasmonic probe.

2. The plasmonic droplet according to claim 1, wherein the droplet of fluid is a droplet of a first fluid which is in an emulsion of the first fluid and a second fluid.

3. The plasmonic droplet according to claim 1, wherein the plasmonic droplet further comprises a layer of a surfactant on the surface of droplet of fluid, and the nanoplasmon probe is on the layer of the surfactant and/or in the droplet of fluid.

4. The plasmonic droplet according to claim 1, wherein two or more plasmoninc droplets are arranged to constitute an array of the plasmonic droplet.

5. A method for preparing a plasmonic droplet, comprising:
    providing a micro-fluid flow of a second fluid with a micro-fluid flow of a first fluid comprising a nanoplasmon probe and a detection-target material, thereby forming a plasmonic droplet,
    wherein the first fluid and the second fluid are able to form an emulsion;
    wherein the plasmonic droplet comprises a droplet of the first fluid; a detection-target material which is in the droplet of the first fluid; and a nanoplasmon probe which is on a surface of the droplet of the first fluid and/or in the droplet of the first fluid; and
    wherein the detection-target material is to be detected by the nanoplasmonic probe.

6. The method according to claim 5, wherein the first fluid further comprises a surfactant.

7. The method according to claim 5, wherein the method further comprises reducing a size of the plasmonic droplet to the extent that the nanoplasmon probe is attached to the detection-target material.

8. The method according to claim 5, wherein the method further comprises changing the size of the plasmonic droplet by changing a pressure of at least one of the micro-fluid of the first flow and the micro-fluid of the second flow.

9. The method according to claim 5, wherein the method further comprises reducing the size of the plasmonic droplet by vaporizing the first fluid in the plasmonic droplet.

10. The method according to claim 5, wherein the diameter of the plasmonic droplet is from about 15 micrometer to about 25 micrometer.

11. The method according to claim 5, wherein the second fluid has an oil phase and the first fluid is $H_2O$.

12. An apparatus for preparing a plasmonic droplet, comprising:
- a second micro-fluid channel guiding a micro-fluid flow of a second fluid; and
- a first micro-fluid channel guiding a micro-fluid flow of a first fluid comprising a detection-target material and a nanoplasmon probe and providing the second micro-fluid channel with the micro-fluid flow of the first fluid,
- wherein the first fluid and the second fluid are able to form an emulsion;
- wherein the plasmonic droplet comprises a droplet of the first fluid; a detection-target material which is in the droplet of the first fluid; and a nanoplasmon probe which is on a surface of the droplet of the first fluid and/or in the droplet of the first fluid; and
- wherein the detection-target material is to be detected by the nanoplasmonic probe.

13. The apparatus according to claim 12, wherein the first fluid further includes a surfactant.

14. A method for detecting target material, comprising:
- providing a plasmonic droplet comprising a droplet of fluid; a detection-target material which is in the droplet of fluid; and a nanoplasmon probe which is on a surface of the droplet of fluid and/or in the droplet of fluid;
- reducing a size of the plasmonic droplet to the extent that the nanoplasmon probe is attached to the detection-target material; and
- performing plasmon based optical sensing with the plasmonic droplet where the nanoplasmon probe is attached to the detection-target material,
- wherein the detection-target material is to be detected by the nanoplasmonic probe.

* * * * *